(12) United States Patent
Denolly

(10) Patent No.: US 7,717,880 B2
(45) Date of Patent: May 18, 2010

(54) DEVICE FOR INFLATING A BALLOON

(75) Inventor: Pascal Denolly, Jardin (FR)

(73) Assignee: Sedat, Irigny (FR)

( * ) Notice: Subject to any disclaimer, the term of this patent is extended or adjusted under 35 U.S.C. 154(b) by 1080 days.

(21) Appl. No.: 10/764,490

(22) Filed: Jan. 27, 2004

(65) Prior Publication Data

US 2004/0247453 A1  Dec. 9, 2004

(30) Foreign Application Priority Data

Jan. 27, 2003  (FR) .................................. 03 00868

(51) Int. Cl.
*A61M 5/315* (2006.01)
(52) U.S. Cl. ...................... 604/228; 604/155
(58) Field of Classification Search ................. 604/155, 604/228, 227, 218, 181, 96.01, 920, 97.01, 604/99.01; 606/192
See application file for complete search history.

(56) References Cited

U.S. PATENT DOCUMENTS

| | | |
|---|---|---|
| 4,832,692 A | 5/1989 | Box et al. |
| 5,147,300 A | 9/1992 | Robinson et al. |
| 5,306,248 A * | 4/1994 | Barrington ................ 604/97.02 |
| 6,106,496 A | 8/2000 | Arnissolle |
| 6,110,151 A * | 8/2000 | Spool et al. .................. 604/218 |
| 6,916,308 B2 * | 7/2005 | Dixon et al. ................. 604/122 |

FOREIGN PATENT DOCUMENTS

EP  565045 A1  10/1993

* cited by examiner

*Primary Examiner*—Brian Casler
*Assistant Examiner*—Deanna K Hall
(74) *Attorney, Agent, or Firm*—Sughrue Mion, PLLC

(57) ABSTRACT

The inflation device comprises a syringe whose piston presents a thread. It further comprises a retaining mechanism for retaining the piston and comprising two half-nuts movable between a position in which they are spaced apart from the thread and a position in which they engage the thread, together with control members mounted to tilt relative to the syringe body. For each half-nut, the retaining mechanism comprises two resilient tabs pressing against the corresponding half-nut and against the syringe body. In addition, each of the control members comprises a finger pressing against the corresponding half-nut and adapted, when the member tilts, to press against one of two bearing surfaces carried by the half-nut and offset relative to each other in a radial direction of the syringe body.

10 Claims, 9 Drawing Sheets

DEVICE FOR INFLATING A BALLOON

The present invention relates to a balloon inflation device of the type comprising a syringe comprising a syringe body and a syringe piston slidably and rotatably displaceable in said syringe body, the piston presenting an outside thread over at least a fraction of its length, the device further comprising a retaining mechanism for retaining the piston and comprising, firstly at least one half-nut movable between a position where it is spaced apart from the thread, and in which the piston is free to slide in the syringe body, and a position where it engages the thread, in which free sliding of the piston is impossible, and in which the piston can be screwed into or out from the syringe body, and secondly, for each half-nut, a control member for controlling the displacement of the corresponding half-nut between its two positions, said member being movably mounted relative to the syringe body.

BACKGROUND OF THE INVENTION

Such inflation devices are used for injecting a fluid into a balloon that has previously been placed, while in the contracted state, inside an artery or a vein of a patient. Such devices are described, for example, in U.S. Pat. No. 5,147,300.

Such devices are used in particular for percutaneous transluminal angioplasty, in particular for the purpose of dilating the artery or the vein in which the balloon is disposed.

Inflation devices must be capable of delivering high pressure, of the order of 30 bars. Under the action of such pressure, the piston is subjected to a large axial force which, in the absence of manual pressure on the free end of the piston, needs to be contained by the half-nut(s) co-operating with the thread.

In addition, particularly when the device has only one half-nut as described in the above-mentioned US patent, the member for controlling said half-nut is formed by a rod whose end is deformed into a crank shape. This end is engaged in a slot of the half-nut so as to cause it to move sideways when the rod is moved axially along the syringe body.

Because of the high pressure that exists inside the syringe, which pressure exerts a high axial thrust force on the piston, releasing the half-nut requires a large amount of force such that the control rod tends to become deformed without performing its function of moving the half-nut in satisfactory manner. It is therefore necessary to make the control member out of a material that is extremely rigid, thereby increasing the cost of manufacturing the device.

In addition, the control rod of that device is moved by drive from one of the practitioner's thumbs on a mechanism for driving the rod in translation. However, it is often difficult to release the half-nut while pressing with one thumb only. In other words, the device is not very ergonomic.

OBJECTS AND SUMMARY OF THE INVENTION

An object of the invention is to provide a balloon inflation device which is more ergonomic to handle, enabling the piston to be engaged and released in a manner that is reliable and easy, while nevertheless making it possible to use ordinary, low-cost materials.

To this end, the invention provides a balloon inflation device of the above-specified type in which the retaining mechanism comprises, for each half-nut, at least one elastically-deformable element pressing against the corresponding half-nut and against the syringe body, and the control member comprises a finger bearing against the corresponding half-nut and adapted, during displacement of the control member, to bear against two surfaces carried by the half-nut and offset from each other in a radial direction of the syringe body, the half-nut being in its position spaced apart from the thread when the finger bears against the surface that is radially closer to the syringe piston, and the half-nut being in its position engaged with the thread when the finger is pressed against the surface that is further away.

According to other characteristics of the device, taken singly or in any technically feasible combination:

- the deformable element is secured to the corresponding half-nut;
- the deformable element is a resilient tab which extends substantially parallel to the longitudinal direction of the syringe body;
- for the or each half-nut there are provided two deformable elements disposed on either side of the half-nut in the longitudinal direction of the syringe body;
- the or each half-nut presents a transition surface passing between the two surfaces against which the corresponding finger presses, said transition surface forming a cam for said finger;
- said surface further away from the syringe piston is provided with a projection suitable for blocking the finger pressed against said surface;
- the control member for the or each half-nut is mounted to tilt about an axis perpendicular to the longitudinal direction of the syringe body;
- the or each control member is received in a housing secured to the syringe body and having said control member movably mounted thereto;
- the or each half-nut comprises a hollow body for receiving a portion of the corresponding finger, which hollow body comprises a bottom wall carrying said two surfaces against which the finger presses, and side walls forming surfaces for guiding the finger during its displacements relative to the syringe body; and
- the retaining mechanism for retaining the syringe piston comprises only one half-nut, and it further comprises a rigid handle integrally molded with the syringe body and situated diametrically opposite the control member for the sole half-nut.

BRIEF DESCRIPTION OF THE DRAWINGS

The invention will be better understood on reading the following description given purely by way of example and made with reference to the drawings, in which.

MORE DETAILED DESCRIPTION

Figure 1A:
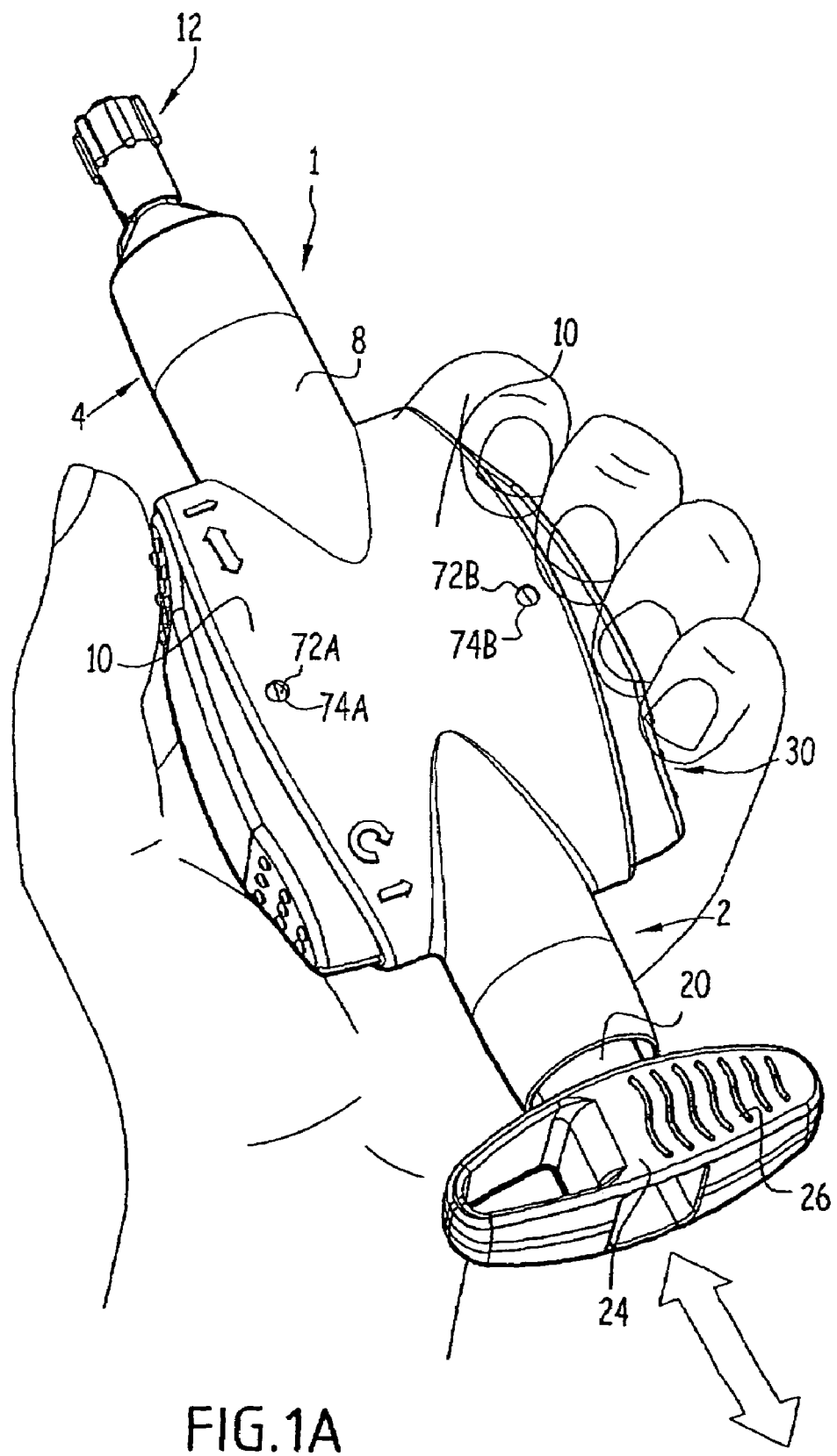
FIGS. 1A and 1B are perspective views of a device of the invention being handled in such a manner as respectively to enable the piston of the syringe to slide and to enable the piston to be screwed in or out.

The device 1 for inflating a balloon shown in FIGS. 1A, 1B, 2, 3A and 3B comprises a syringe 2 extending along an axis X-X and comprising essentially a syringe body 4 and a piston 6. The capacity of the syringe is advantageously 30 cubic centimeters ($cm^3$).

The syringe body 4 which is made of transparent plastics material comprises a tubular portion 8 having two lateral housings 10 disposed on diametrically-opposite sides thereof and molded integrally with the tubular portion.

The front end of the syringe body, i.e. its smaller-diameter end is provided with a coupling assembly 12 adapted to releasably receive a connector of complementary shape (not shown). This coupling assembly, commonly referred to as a "rotating coupling" includes a deformable member 14 for retaining the connector, and sealing means 16, e.g. formed by a gasket.

The syringe piston 6 is formed by a rod 20 provided at its end received inside the tubular portion 8, through the rear end of the syringe body 4, with a head 22 that slides in leaktight manner inside the syringe body 4. At its other end, the rod carries a handle 24 for actuating the piston 6 manually. This handle is provided with a non-slip covering 26 to make it easier to hold in the hand.

The rod 20 is provided on the outside with a thread 28 over at least a fraction of its length.

Figure 2:
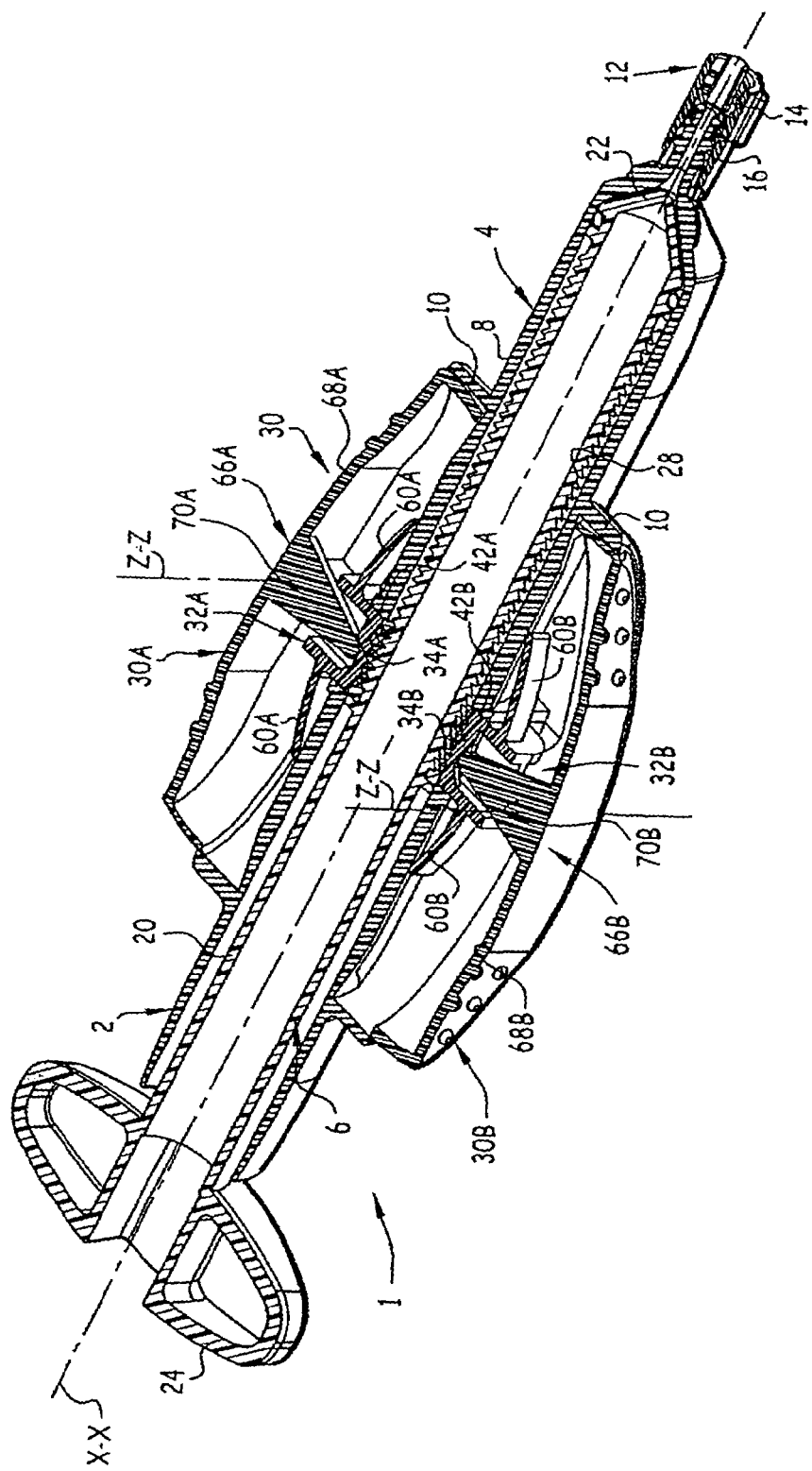
FIG. 2 is a perspective view in longitudinal section on a midplane of the device in FIG. 1A.
Figure 3A:
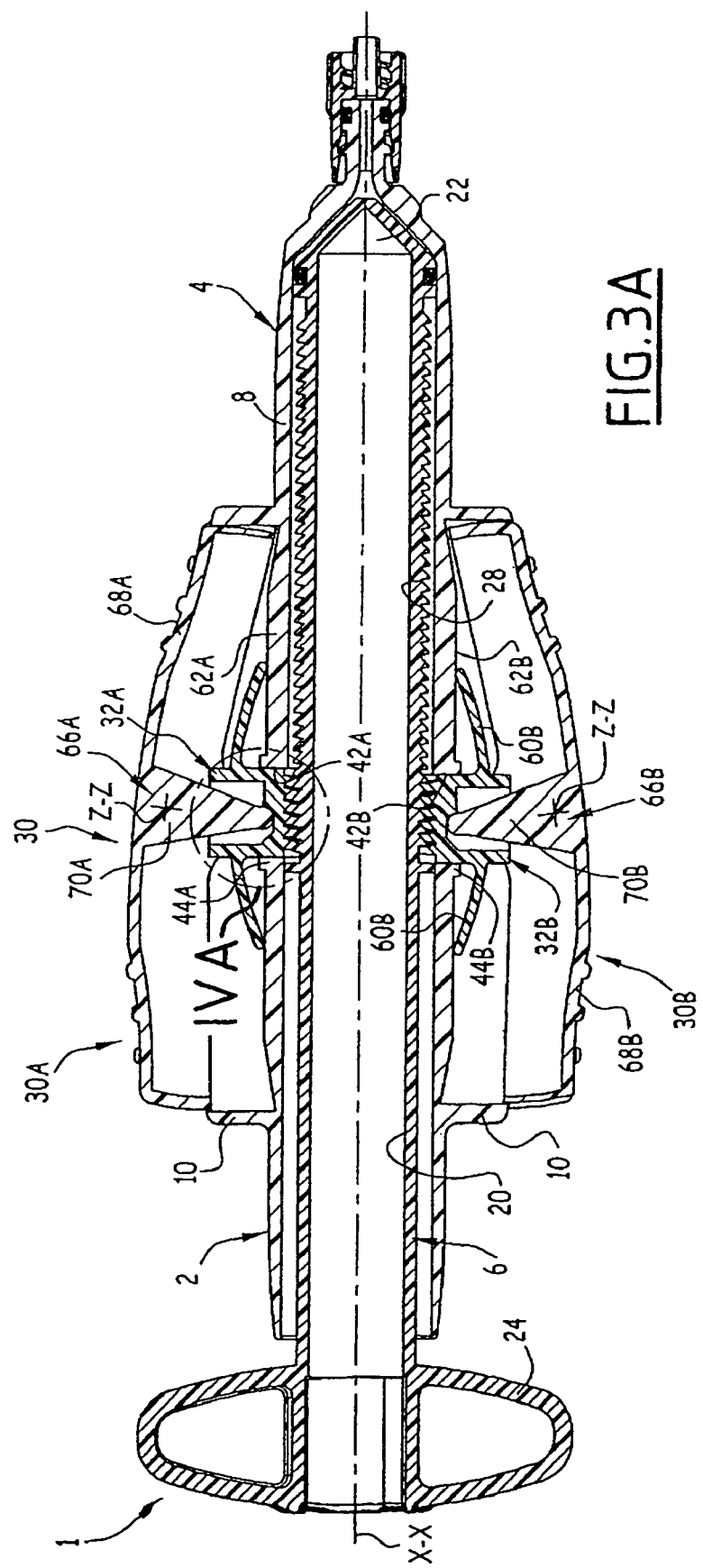
FIGS. 3A and 3B are plane section views on the same section plane as FIG. 2, respectively showing the device of FIG. 1A and the device of FIG. 1B.
Figure 3B:
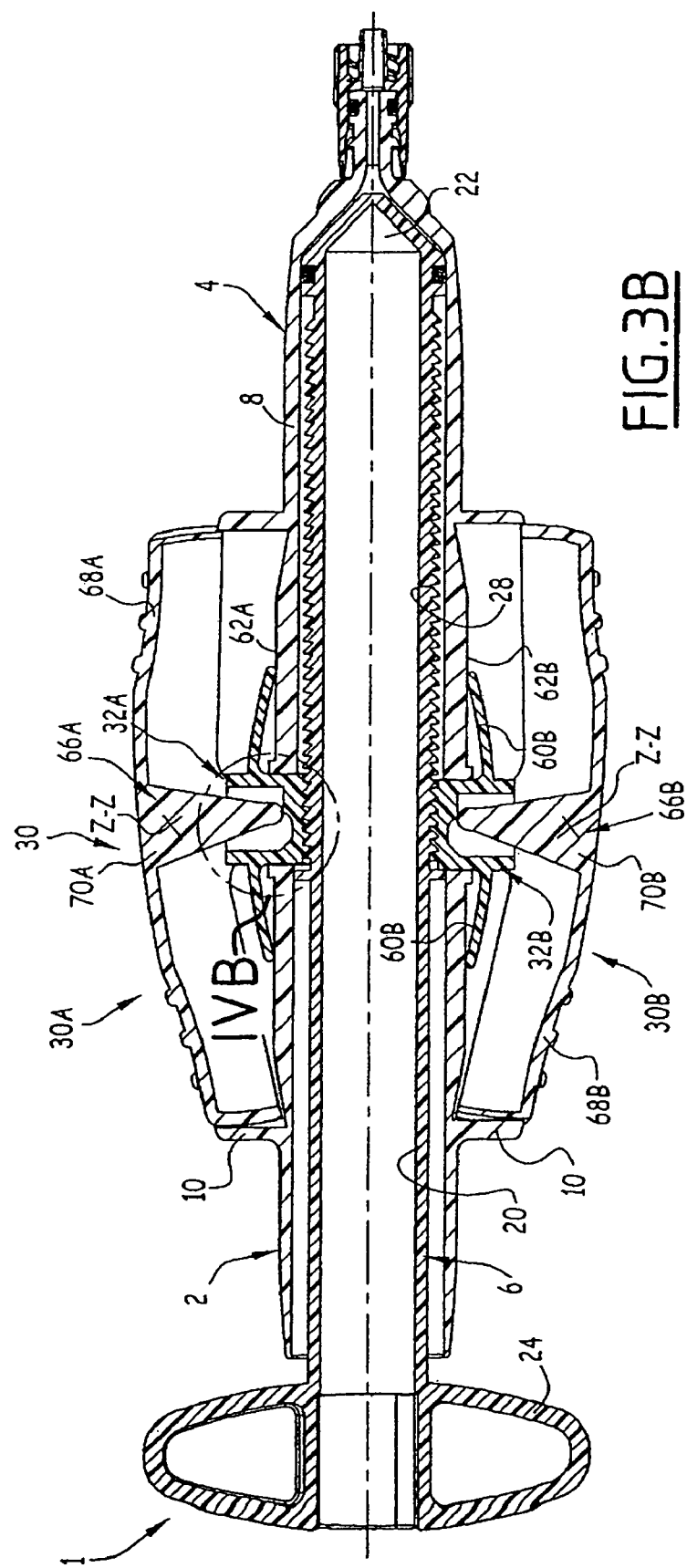

The device 1 also comprises a mechanism 30 for retaining the piston 6, which mechanism is received for the most part inside the lateral housings 10. As shown in FIGS. 2, 3A, and 3B, this mechanism comprises two identical assemblies 30A and 30B each received in a respective lateral housing, symmetrically about a midplane perpendicular to the section plane of FIG. 2. The detailed description below thus refers only to the assembly 30A, with it being understood that the assembly 30B has the same elements as the assembly 30A and that elements that are identical in the two assemblies are given the same numerical references followed by the letter A for the assembly 30A or by the letter B for the assembly 30B.

Figure 4A:
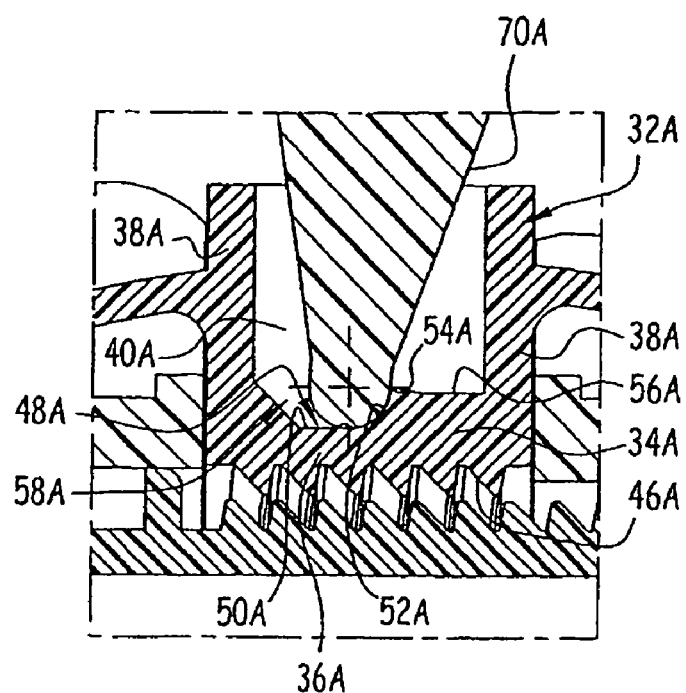
FIGS. 4A and 4B are larger-scale views of the encircled details referenced IVA and IVB respectively in FIGS. 3A and 3B.
Figure 4B:
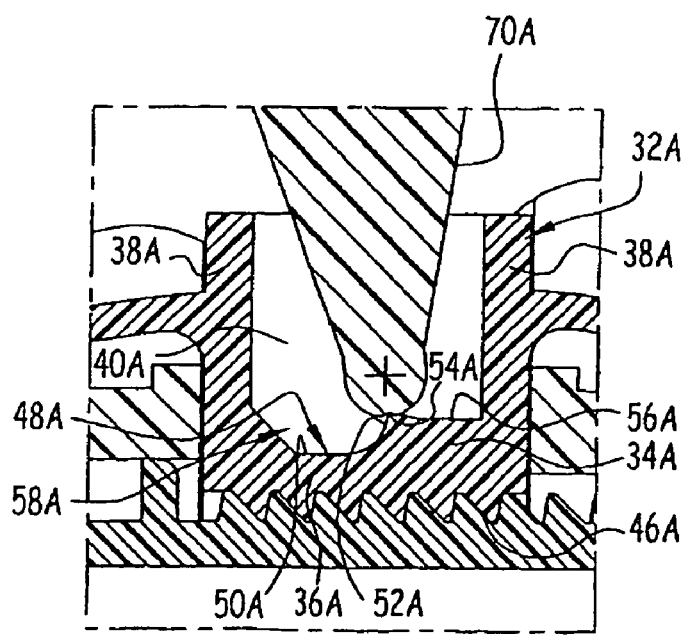
Figure 5:
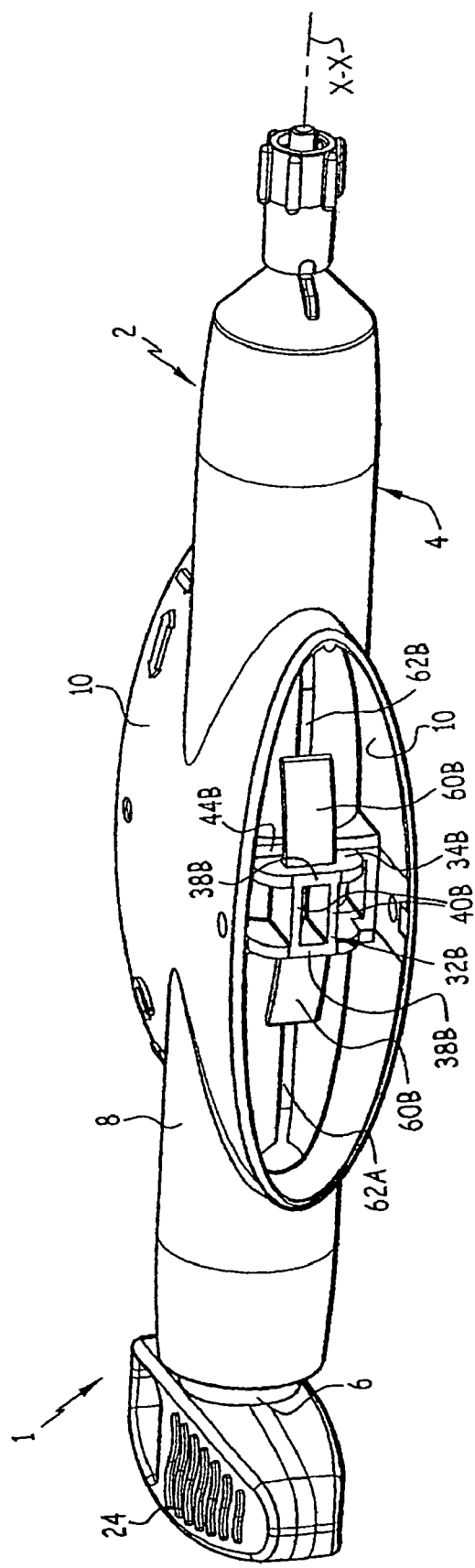
FIG. 5 is a perspective view of the FIG. 2 device, with the members for controlling displacement of the half-nuts not being shown.

The retaining assembly 30A comprises a half-nut 32A presenting a hollow body 34A shown in greater detail in FIGS. 4A, 4B, and 5. This body is essentially formed by a bottom wall 36A which extends parallel to the piston of the syringe 6, two opposite side walls 38A which extend substantially perpendicularly to the axis X-X of the syringe, and two opposite side walls 40A interconnecting the walls 30A, with only one of these walls 40A being visible in FIGS. 2, 3A, 3B, 4A, and 4B.

The half-nut 32A is received inside an oblong through opening 42A formed in the tubular portion 8 of the syringe body 4, and it is held therein by a housing bracket 44A secured to the syringe body 4, e.g. integrally molded with the tubular portion 8 and the housings 10. This bracket 44A is ribbed firstly to allow the half-nut to move in a direction substantially perpendicular to the axis X-X and contained in the section plane of FIG. 2, and secondly to block the half-nut both in directions that are parallel to the axis X-X, and in other directions that are perpendicular to said axis.

The bottom wall 36A of the half-nut 32A presents a tapped surface 46A on its side facing towards the inside of the syringe body 4, and designed to engage the thread 28 on the piston 6.

Figure 1B:
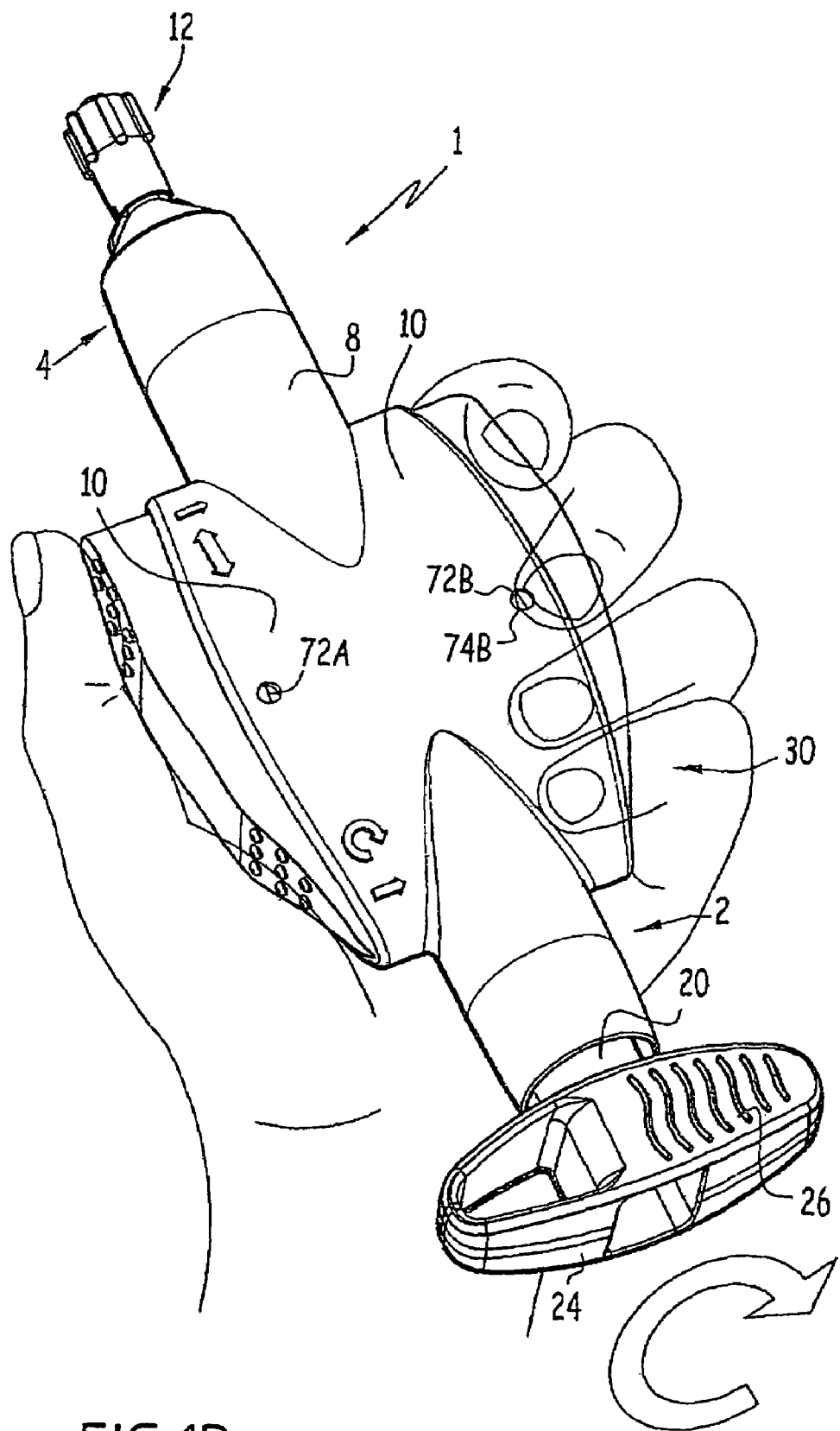

The half-nut can thus be moved between a position where it is spaced apart from the thread 28, as shown in FIGS. 1A and 3A, and in which the piston 6 is free to slide in the syringe body 4, and a position in which it engages the thread, as shown in FIGS. 1B and 3B, and in which the piston 6 can be screwed in or out of the syringe body 4, while being prevented from sliding freely.

The bottom wall 36A of the half-nut 32A also presents a stepped face 48A on its side facing towards the outside of the syringe body 4, and shown in detail in FIGS. 4A and 4B. This face comprises in succession, from back to front: a first substantially plane surface 50A; a ramp-forming surface 52A sloping outwards; a rim 54A of rounded shape and projecting outwards; and, setback inwards relative to the top of the rim 54A, a second substantially plane surface 56A that is further away from the syringe axis X-X than is the first surface 50A. In FIGS. 4A and 4B, the respective proportions of the surfaces 50A, 52A, and 56A and of the rim 54A are exaggerated to make them more visible.

The retaining assembly 30A also comprises two elastically-deformable tabs 60A which extend on either side of the half-nut 32A along the axis X-X. These tabs 60A are integrally molded with the side walls 38A of the body 34A of the half-nut. The free ends of these tabs bear resiliently against a longitudinal rib 62A formed along the tubular portion 8 of the syringe body.

As shown in FIGS. 2, 3A, and 3B, the retaining assembly 30A further comprises a control member 66A for controlling the displacement of the half-nut 32A and made entirely out of molded plastics material. This member comprises a half-shell 68A whose internal recess faces towards the syringe body 4, and a finger 70A of generally pyramid-shape with its base formed integrally with the half-shell.

The half-shell 68A forms a cover for closing the corresponding housing 10, being movable relative thereto. More precisely, as shown in FIGS. 1A and 1B, two cylindrical pegs 72A (only one is visible in FIGS. 1A and 1B) of axis Z-Z perpendicular to the section plane of FIGS. 2, 3A, and 3B, are formed projecting from the finger 70A, each then extending from one of the two sides of the finger 70A that extends substantially parallel to the section plane of FIG. 2. These pegs are received in substantially complementary openings 74A formed in the wall of the housing 10. As a result, the control member 66A can be tilted about the axis Z-Z relative to the syringe body 4.

The finger 70A is adapted to be received inside the hollow body 34A of the half-nut 32A and to press against the stepped face 48A of said half-nut. More precisely, when the control member 66A is tilted forwards, as shown in FIGS. 1A, 3A, and 4A, the free end of the finger 70A bears against the surface 50A, with the resilient tabs 60A holding the half-nut in the spaced-apart position, in such a manner that the piston 6 is free to slide. When the member 66A is tilted rearwards, as shown in FIGS. 1B, 3B, and 4B, the finger 70A comes to bear against the surface 56A and the resilient tabs 60A are deformed so that the half-nut 32A engages the thread 28 of the piston, thus ensuring that it can be moved only by being screwed in or out.

Movements of the finger are guided, and possibly also limited, by the inside faces of the side walls 38A and 40A of the hollow body 34A. By way of example, for the device shown, the tilt angle formed by the finger about the axis Z-Z is about 12°.

The inflation device 1 operates as follows:

In order to inflate a balloon, the operator connects the front end of the device 1 to a balloon, e.g. via a tubular fitting provided at its outside end with a connector, by fastening the connector to the assembly 12.

Thereafter, the operator takes hold of the device in the manner shown in FIG. 1A, i.e. pressing the front portions of the half-shells 68A and 68B together manually, in particular between thumb and index finger so as to cause the control members 66A and 66B to tilt forwards. The operator can then push the piston rod 6 into the inside of the syringe body 4 so as to increase the pressure of the fluid contained in the syringe, until a pressure of about 3 bars is reached, which corresponds in general to the pressure that can be obtained merely by pushing on the piston.

After that, the operator tilts the control members 66A and 66B rearwards, as shown in FIG. 1B, by exerting manual pressure on the rear portions of the half-shells, in particular by pressing the half-shells together between the ball of the thumb and the little finger. By tilting the control members rearwards, the ends of the fingers 70A, 70B are caused to move away from the surfaces 50A, 50B and to the surfaces 56A, 56B. As they move, these ends press against the ramps 52A and 52B, thereby delivering a cam effect causing the thread 28 to be engaged by the half-nuts 32A and 32B.

The operator then continues to raise pressure by progressively screwing the piston into the syringe body up to a pressure that may be as great as 30 bars, for example. The half-nuts 32A and 32B are held firmly engaged with the thread of the piston by the fingers 70A and 70B, the rims 54A and 54B of the stepped faces 48A and 48B of the half-nuts ensuring that the control members are held in the rearwardly-tilted position.

The half-nuts are subsequently released by performing the above-described steps in the reverse order.

In the syringe described herein, the presence of two half-nuts 32A and 32B in a symmetrical disposition avoids any bending of the rod 20 of the piston 6.

In addition, the half-nuts are caused to engage and disengage the thread 28 of the piston 6 by tilting the control members 66A and 66B by gripping the device in the hand in ergonomic manner. Unlike prior art devices, these tilting movements are obtained by manually squeezing a portion of the device that is held in the hollow of one hand of the user, with the user then being able to exert a force that is greater than that which can be obtained, e.g. by pushing with the thumb only.

In addition, the number of component parts of the device is small, since the lateral housings for receiving the retaining assemblies 30A, 30B are formed integrally with the syringe body. Manufacturing and assembly costs for the device are therefore low.

Figure 6:
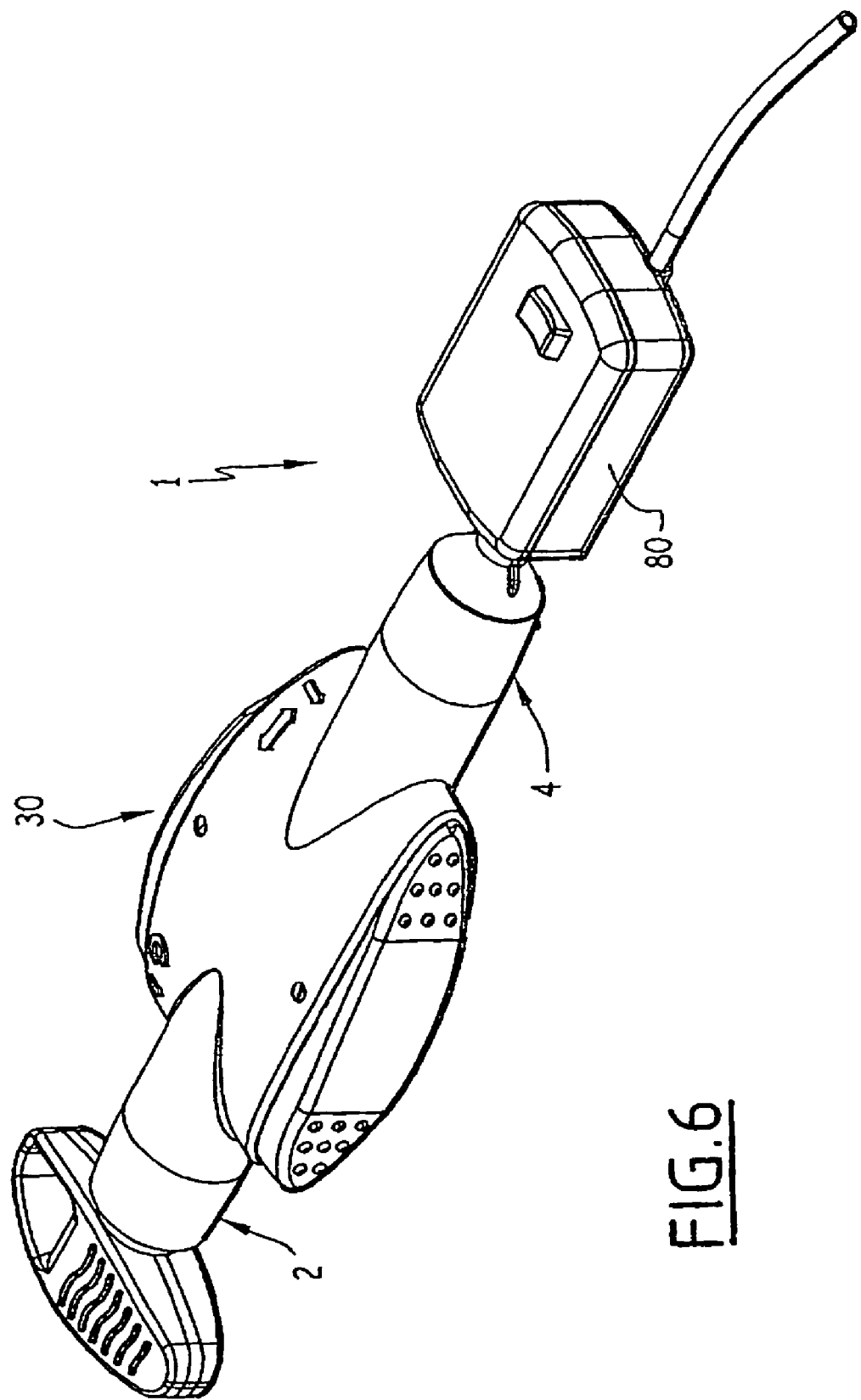
FIG. 6 is a perspective view of the FIG. 1 device provided with a pressure gauge.

In addition, the coupling assembly 12 carried at the front end of the device 1 makes it possible to install a tube fitting with offset pressure measurement and/or with a pressure gauge 80, which gauge can equally well be of the mechanical type having an indicator needle or of the electronic type with a pressure sensor, as shown in FIG. 6.

Since the pressure gauge is removable, it can be reused. In addition, various types of pressure gauge can be used with a single type of balloon inflation device.

Figure 7:
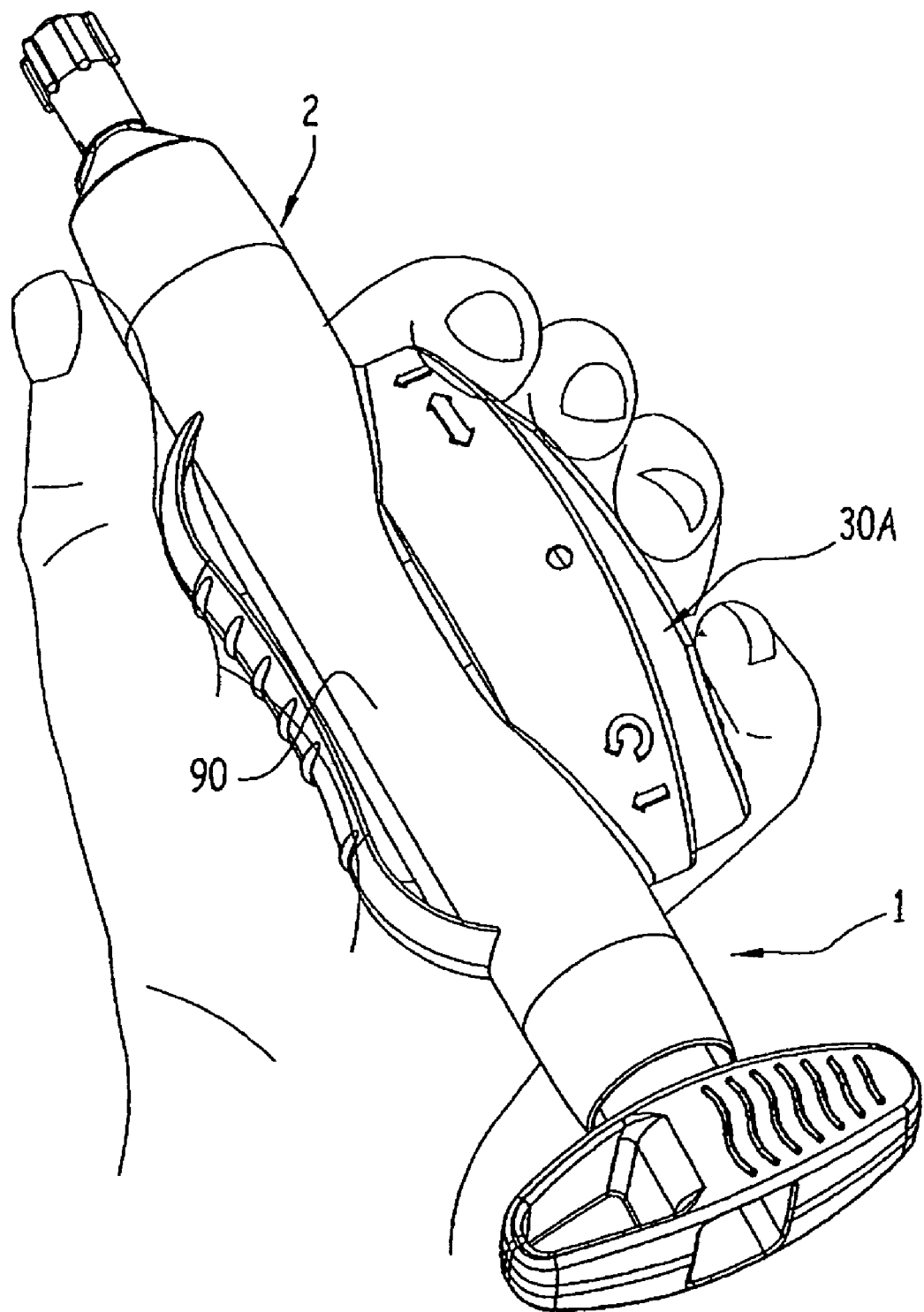
FIG. 7 is a perspective view of a variant device of the invention.

FIG. 7 shows a variant of the device 1 which differs from the device of the preceding figures in that its mechanism for retaining the syringe piston is formed by a single assembly 30A. On the side of the syringe body 4 opposite from said assembly 30A, the device has an ergonomically-shaped handle 90 which is advantageously integrated in the syringe body 4.

This variant operates in a manner identical to that described above.

Other arrangements and variants of the above-described devices can be envisaged:

rigid plates extending perpendicularly to the side walls 38A, 38B and the resilient tabs 60A, 60B can be replaced by resilient abutments, e.g. springs, disposed between the free ends of each of said plates and the tubular portion 8 of the syringe body; and/or the profile of the stepped faces 48A, 48B against which the fingers 70A, 70B press presents indentations and/or projections adapted to make it easier to block and release the ends of the fingers when the control members are tilted.

What is claimed is:

1. A balloon inflation device of the type comprising
   a syringe, extending between a front and a back thereof along a syringe axis, comprising
   a syringe body and
   a syringe piston slidably and rotatably displaceable in said syringe body,
      the piston presenting an outside thread over at least a fraction of its length, the device further comprising a retaining mechanism for retaining the piston and comprising,
      firstly at least one half-nut movable between
         a position where it is spaced apart from the thread, and in which the piston is free to slide in the syringe body, and
         a position where it engages the thread, in which free sliding of the piston is impossible, and in which the piston can be screwed into or out from the syringe body, and
      secondly, for each half-nut, a control member for controlling the displacement of the corresponding half-nut between its two positions, said member being movably mounted relative to the syringe body,
   wherein the retaining mechanism comprises,
      for each half-nut, at least one elastically-deformable element pressing against the corresponding half-nut and against the syringe body, and wherein the control member comprises a finger bearing against the corresponding half-nut and adapted, during displacement of the control member, to bear against two surfaces carried by the half-nut,
      the two surfaces being arranged in succession longitudinally along the syringe axis from the back to the front thereof and offset from each other in a radial direction of the syringe body,
      the half-nut being in its position spaced apart from the thread when the finger bears against the surface that is radially closer to the syringe piston, and
      the half-nut being in its position engaged with the thread when the finger is pressed against the surface that is further away.

2. A device according to claim 1, wherein the deformable element is secured to the corresponding half-nut.

3. A device according to claim 1, wherein the deformable element is a resilient tab which extends substantially parallel to the longitudinal direction of the syringe body.

4. A device according to claim 1, wherein, for the or each half-nut there are provided two deformable elements disposed on either side of the half-nut in the longitudinal direction of the syringe body.

5. A device according to claim 1, wherein the or each half-nut presents a transition surface passing between the two surfaces against which the corresponding finger presses, said transition surface forming a cam for said finger.

6. A device according to claim 1, wherein said surface further away from the syringe piston is provided with a projection suitable for blocking the finger pressed against said surface.

7. A device according to claim 1, wherein the control member for the or each half-nut is mounted to tilt about an axis perpendicular to the longitudinal direction of the syringe body.

8. A device according to claim 1, wherein the or each control member is received in a housing secured to the syringe body and having said control member movably mounted thereto.

9. A device according to claim 1, wherein the or each half-nut comprises a hollow body for receiving a portion of the corresponding finger, which hollow body comprises a bottom wall carrying said two surfaces against which the finger presses, and side walls forming surfaces for guiding the finger during its displacements relative to the syringe body.

10. A device according to claim 1, wherein the retaining mechanism for retaining the syringe piston comprises only one half-nut, and wherein the device further comprises a rigid handle integrally molded with the syringe body and situated diametrically opposite the control member for the sole half-nut.

* * * * *